United States Patent [19]

Ovchinnikov et al.

[11] Patent Number: 4,642,354
[45] Date of Patent: Feb. 10, 1987

[54] PROCESS FOR PRODUCING PHTHALIMIDES OF ALKALI METALS

[75] Inventors: Alexandr A. Ovchinnikov; Vladimir P. Dudin; Vyacheslav V. Konov; Vyacheslav I. Khlybov; Jury M. Rapoport; Boris N. Gorbunov; Evgenia S. Makarova; Valentin V. Davituliani; Svetlana I. Zaitseva, all of Tambov, U.S.S.R.

[73] Assignee: Nauchno-Issledovatelsky Institut Khimikatov Dlya Polimernykh Materialov, Tambov, U.S.S.R.

[21] Appl. No.: 776,112
[22] PCT Filed: Jan. 23, 1984
[86] PCT No.: PCT/SU84/00003
§ 371 Date: Aug. 26, 1985
§ 102(e) Date: Aug. 26, 1985
[87] PCT Pub. No.: WO85/03292
PCT Pub. Date: Aug. 1, 1985

[51] Int. Cl.$^4$ .................................. C07D 209/48
[52] U.S. Cl. .................................... 548/473
[58] Field of Search ........................... 548/473

[56] References Cited

FOREIGN PATENT DOCUMENTS 1420523 1/1976 United Kingdom .

OTHER PUBLICATIONS

N. N. Suvorov (ed.), Weigand-Hilgetag, Experimental Methods in Organic Chemistry (translation from 3-d German edition), Moscow, "Khimiya" publishers, p. 415 (1968).

Primary Examiner—Donald G. Daus
Assistant Examiner—Mary E. Ceperley
Attorney, Agent, or Firm—Burgess, Ryan & Wayne

[57] ABSTRACT

A process for producing phthalimides of alkali metals by reacting phthalimide with an alcoholic solution of an alkali metal hydroxide and/or alcoholate, in which the molar ratio is equal to 1:1.03–1.1, while maintaining the alcohol concentration in the reaction mass within the range of from 10 to 60% by mass.

11 Claims, No Drawings

PROCESS FOR PRODUCING PHTHALIMIDES OF ALKALI METALS

FIELD OF THE ART

The present invention relates to the organic synthesis of and, more particularly, to a process for producing phthalimides of alkali metals.

DESCRIPTION OF THE PRIOR ART

Known in the art is a process for producing potassium phthalimide by reacting a 5% solution of phthalimide in absolute ethanol with a 25% ethanolic solution of potassium hydroxide. After decanting the solutions the reaction mass is rapidly cooled, filtered-off to remove the formed potassium phthalimide, the precipitate is then suspended in acetone, filtered and dried in air with moderate heating to give about 90% of the product (Experimental Methods in Organic Chemistry, Moscow, "Khimiya" Publishing House, 1969, p. 415).

This prior art process features a low yield of the desired product, a considerable rate of consumption of ethanol and acetone; the process is also characterized by the use of explosive and flammable solvents.

Also known in the art is a process for the production of phthalimides of alkali metals by reacting a suspension of a finely-divided phthalimide in dehydrated aliphatic alcohols containing 1 to 4 carbon atoms in a molecule with a solution of an alkali metal hydroxide or alcoholate in the same alcohols. The process is conducted at a temperature within the range of from 35° to 50° C. for a period of 1 to 6 hours. After residence for a certain period the suspension is cooled to 20° C., the precipitate is washed with alcohol and dried. The yield of the desired product is 85% (cf. British Pat. No. 1,420,523 Cl. C 2 C, published 1976).

As can be seen, this process also features a low yield of the desired product. Also known is a process for producing phthalimides of alkali metals, consisting of adding
a mixture of solutions of an alkali metal butylate and hydroxide in an organic solvent in a molar ratio of the alkali metal butylate to the alkali metal hydroxide equal to 0.5:0.5–0.99:0.01 by metering to a suspension of phthalimide in an organic solvent at a temperature of from 50° to 110° C. for 60–70 minutes. The synthesis is carried out in a vessel provided with a stirrer and a reflux condenser to recycle the solvent vapours. After complete intermixing of the reactants the reaction mass is kept for 20 minutes, cooled, filtered, and dried. To prepare a suspension of phthalimide, butanol, benzene, chlorobenzene, or white-spirit is used as an organic solvent. For the preparation of a solution of an alkali metal butylate or alkali metal hydroxide, butanol or its mixture with the above-mentioned solvents is used. The product yield is equal to 97–99%, the content of the main substance is 95–99% (cf. USSR Inventor's Certificate No. 87594, Int. Cl. C 07 D 209/48, published 1982).

This process features rather complicated and lasting auxiliary stages of filtration and drying of the product to remove the organic solvent. The suspension of the product, obtained in the above-described manner, is unsatisfactorily filtered, the precipitate is unsatisfactorily pressed and, hence, contains a considerable percentage (50–70%) of the solvent. The filtered-off cake is liable to a thixotropic liquefaction under the effect of mechanical loads; it adheres to metal surfaces, thus appreciably hindering transportation of the slurry from the filter to the drier. The adherence of the product to the walls and rotor of the vacuum-scraper drier complicates the drying process, makes it time consuming and less effective. The duration of the drying stage is 5–6 hours, and that of the entire process is 6.5 to 8.5 hours.

DESCRIPTION OF THE INVENTION

It is an object of the present invention to provide such a process for producing phthalimides of alkali metals, which would be more simple in practical implementation.

This object is accomplished by the production of phthalimides of alkali metals by way of interaction of a phthalimide with an alcoholic solution of an alkali metal hydroxide and/or an alkali metal alcoholate at a temperature within the range of from 50° to 100° C. In accordance with the present invention, a phthalimide and an alkali metal hydroxide and/or an alkali metal alcoholate is used in an amount ensuring their molar ratio equal to 1:1.03–1.1; the process is conducted under a residual pressure of from 0.07 to 0.005 MPa, and the above-mentioned interaction of the starting components is conducted while maintaining the alcohol concentration in the reaction mass within the range of from 10 to 60% by mass.

According to the present invention, it is advisable that the concentration of the alcohol in the reaction mass be maintained at a level of 10 to 60% by mass by way of removal of the evolved vapours of the alcohol and water from the reaction mass.

The process according to the present invention makes it possible to substantially intensify and simplify
production, eliminate the stages of filtering the suspension and drying the paste, avoid the between-operation transportation of a sticky staining paste and avoid the use of sophisticated process equipment. The duration of the process for the production of phthalimides of alkali metals is reduced from 6–8 hours to 1.5–3.5 hours.

BEST MODE OF CARRYING THE INVENTION INTO EFFECT

The process for producing phthalimides of alkali metals according to the present invention can be carried out in mixers suitable for agitation of paste-like products, for example, in mixers of the Werner-Pfleiderer type. The process is conducted at a temperature of from 50° to 100° C., preferably at a temperature of 70°–80° C. At a temperature of the reaction mass above 100° C. the content of the basic substance in the desired product is reduced, while at a temperature less than 50° C. the process duration is extended and the product quality is lowered. Phthalimide as well as the alkali metal hydroxide and/or alcoholate are used in amounts ensuring their molar ratio of 1:1.03–1.10 respectively. When less than 1.03 moles of the alkali metal hydroxide and/or alcoholate are used, the resulting desired product is unstable in storage. The use of more than 1.1 moles of the alkali metal hydroxide and/or alcoholate is undesirable, since it results in a lowered content of the main substance in the desired product due to a mechanical dilution of the latter with a free alkali.

As the organic solvent for the preparation of a solution of an alkali metal hydroxide and/or alcoholate, aliphatic alcohols containing 1 to 4 carbon atoms in a molecule are used. The alcoholic solution is gradually fed, under stirring, into a mixer containing a phthalimide preheated to a temperature of 50°–100° C. Vapours of the alcohol and water evolving during the interaction are removed from the reaction zone so as to create a residual pressure of 0.07–0.005 MPa in the mixer.

Under a pressure above 0.07 MPa in the mixer the desired product becomes contaminated with by-products by as much as about 15% of its mass due to an insufficiently intensive removal of water vapours and the occurring hydrolysis of the desired product. Under a pressure of below 0.005 MPa due to very intensive evaporation of the alcohol, the interaction between the phthalimide and the alkali metal hydroxide and/or alcoholate proceeds incompletely and the desired product also becomes considerably contaminated. The feed rate of the alcoholic solution and the removal rate of the vapours of the alcohol and water are controlled so that the content of the alcohol in the reaction mass during the period of interaction of the starting components be equal to 10–60% by mass, preferably to 30–40% by mass. When this condition is observed, no adherence of the reaction mass to the reactor walls and impeller blades, or aggregation of particles of the desired product particles occurs. On completion of metering the alcoholic solution, excess alcohol is distilled-off from the reaction mass to a content of the volatiles not more than 0.5%, and then the thus-prepared final product is cooled down to room temperature.

The desired product is obtained in the form of a dry finely divided powder containing 95–99% of the main substance. The product yield is quantitative.

For a better understanding of the present invention some specific examples illustrating its embodiments are given hereinbelow by way of illustration.

EXAMPLE 1

Into a 1.5 l Werner-Pfleiderer mixer provided with a heating jacket, a sealed lid with an inlet pipe for charging the reactants and an outlet pipe for evacuation of vapours, a cooler and a condensate receiver 294.26 g (2 moles) of phthalimide are charged and heated to the temperature of 75° C. while stirring. The reaction mass temperature is measured by means of a chromel-copel thermocouple secured to the mixer lid and immersed into the reaction mass. To the heated phthalimide is added, while stirring, a solution consisting of 115.59 g (2.06 moles) of potassium hydroxide and 650 g of butanol; the solution is supplied at the rate of 15 g/min . At the same time, the pressure in the mixer is maintained at 0.03–0.05 MPa. Vapours of butanol and water evolving during the reaction of phthalimide with potassium hydroxide are condensed in a cooler and collected in a receiver. In the course of supplying the alcoholic solution and distilling-off butanol, the reaction mass is maintained at a temperature of 70°–75° C. When these conditions are observed, the reaction mass during the supply of the solution is a plastic paste which contains 35–40% of butanol. By the end of metering the butanolic solution 400–450 g of butanol are distilled-off from the reaction mass. The residual butanol is distilled-off for 40–50 minutes at a temperature of 70°–75° C., the reaction mass is allowed to stand for 10–20 minutes and is then cooled to 20°–30° C. The distilled-off butanol is regenerated and used in the next operation.

374.22 g of a fine-crystalline white powder are thus obtained, containing 98.5% of the main substance and 0.3% of volatile compounds. The product yield is 99.5% of the theoretical value as calculated for 100% of potassium phthalimide. The process duration is 100–120 minutes.

EXAMPLE 2

294.26 g (2 moles) of phthalimide are charged into a mixer, the mixer is sealed, and phthalimide is heated to 100°–105° C. while stirring; the residual pressure in the mixer is set at 0.05–0.07 MPa, and a solution containing 115.59 g (2.06 moles) of potassium hydroxide and 650 g of butanol is fed thereto at a rate of 17–18 g/min. During the metering of the solution and distilling-off of butanol the reaction mass temperature is maintaining at 95°–100° C.; the reaction mass is a fluid paste containing 10–15% of butanol. By the end of metering 580–610 g of butanol are distilled-off. The remaining butanol is distilled-off under stirring for 20–30 minutes, then the mass is allowed to stand for 10 minutes, and is then cooled to 20°–30° C.

378.26 g of a white powder are thus obtained; the product contains 95% of the main substance and 0.2% of volatile compounds. The product yield is 97% as calculated for 100% of potassium phthalimide.

The process duration is 75–85 minutes.

EXAMPLE 3

294.26 g (2 moles) of phthalimide are charged into a mixer the mixer is sealed, phthalimide is heated to a temperature of 55°–60° C. while stirring, the residual pressure in the mixer is set at 0.0050.01 MPa, and a solution consisting of 115.59 g (2.06 moles) of potassium hydroxide and 650 g of butanol is added thereto. In the course of metering the solution and distilling-off butanol the reaction mass temperature is maintained at 50°–55° C. By the end of metering 150–200 g of butanol are distilled-off from the reaction mixture which is a paste containing 55–60% of butanol. On completion of metering the remaining butanol is distilled-off from the reaction mass, the latter is allowed to stand for 30 minutes, and is then cooled to 20°–30° C.

366.67 g of a white powder are thus obtained said powder containing 98% of the main substance and 0.5% of volatile compounds. The product yield is 97.5% as calculated for 100% of potassium phthalimide.

The process duration is 210–220 minutes.

EXAMPLE 4

Under conditions similar to those described in Example 1 from 294.26 g (2 moles) of phthalimide and 731.17 g of a solution containing 231.17 g (2.06 moles) of potassium butylate and 500 g of butanol and heated to the temperature of 70° C. 373.45 g of a white powder are obtained, said powder containing 99.1% of the main substance and 0.5% of volatile compounds. The product yield is 99.9% as calculated for 100% of potassium phthalimide.

EXAMPLE 5

Under conditions similar to those described in Example 1 hereinbefore, from 294.26 g (2 moles) of phthalimide and 771.37 g of a solution consisting of 109.81 g (1.96 moles) of potassium hydroxide, 11.22 g (0.1 mole) of potassium butylate and 650 g of butanol 372.7 g of a white powder are obtained said powder containing 99.3% of the main substance and 0.1% of volatile compounds.

The product yield is 99.9% as calculated for 100% of potassium phthalimide.

EXAMPLE 6

Under conditions similar to those described in Example 1, from 294.26 g (2 moles) of phthalimide and a solution of 82.4 g (2.06 mol) of sodium hydroxide in 600 g of butanol 346.95 g of a white powder are obtained, containing 97% of sodium phthalimide and 0.3% of volatile components.

The product yield is 99.5% as calculated for 100% of sodium phthalimide.

EXAMPLE 7

Under conditions similar to those described in Example 1 hereinbefore, from 294.26 g (2 moles) of phthalimide and 115.59 g (2.06 moles) of potassium hydroxide dissolved in 650 g of ethanol 374.27 g of a white powder are obtained, said powder containing 97% of the main substance and 0.3% of volatile compounds.

The product yield is 98% as calculated for 100% of potassium phthalimide.

EXAMPLE 8

Under conditions similar to those described in Example 1, from 294.26 g (2 moles) of phthalimide and 115.59 g (2.06 moles) of potassium hydroxide dissolved in 650 g of isopropanol 372.35 g of a white powder are obtained, said powder containing 98% of the main substance and 0.1% of volatile compounds.

The product yield is 98.5% as calculated for 100% of potassium phthalimide.

EXAMPLE 9

Under conditions similar to those described in Example 1, from 294.26 g (2 moles) of phthalimide and 117.8 g (2.10 moles) of potassium hydroxide dissolved in 650 g of butanol 380.1 g of white powder are obtained, said powder containing 96.5% of the main substance and 0.51% of volatile compounds.

The product yield is 99.5% as calculated for 100% of potassium phthalimide.

EXAMPLE 10

Under conditions similar to those described in Example 1, from 294.26 g (2 moles) of phthalimide and 123.4 g (2.2 moles) of potassium hydroxide dissolved in 650 g of butanol 380.5 g of a white powder are obtained, said powder containing 96.4% of the main substance and 0.36% of volatile compounds.

The product yield is 99% as calculated for 100% of potassium phthalimide.

Therefore, the process for producing phthalimides of alkali metals according to the present invention makes it possible to substantially simplify and intensify the production procedure, obviate the stages of filtering the suspension and drying the paste, considerably simplify the process equipment and avoid the between-operation transportation of a sticky staining paste. The duration of the production process is reduced from 6–8 hours to 1.5–3.5 hours.

INDUSTRIAL APPLICABILITY

The present invention will find application in the production of prevulcanization retarders for rubber mixes, dyestuffs, plant protection agents and plarmaceuticals for farm animals, as well as stabilizers and fire-preventing agents for polymeric materials.

What is claimed is:

1. A process for producing alkali metal phthalimides which comprises:
    reacting in a mixture, phthalimide and a solution of at least one member selected from the group consisting of alkali metal hydroxides and alkali metal alcoholates in an alcohol having 1 to 4 carbon atoms, at a temperature of from 50° to 100° C., at a pressure of from 0.07 to 0.005 MPa, wherein the alcohol is present at from about 10% to 60% by weight of the mixture.

2. The process of claim 1 wherein the alcohol is present at from about 30 to 40% by weight of the mixtures.

3. The process of claim 1 wherein the reaction temperature is about 70° to 80° C.

4. The process of claim 2 wherein the temperature is from about 70° to 80° C.

5. A process for producing alkali metal phthalimides which comprises:
    (a) introducing phthalimide into a mixing zone wherein the phthalimide is maintained at a temperature of from 50° to 100° C. under a pressure of from 0.07 to 0.005 MPa,
    (b) introducing into the mixing zone, a solution of at least one alkali metal selected from the group consisting of alkali metal hydroxides and alkali metal alcoholates in an alcohol having 1 to 4 carbon atoms, at a rate to maintain the concentration of alcohol in the mixing zone at from about 10 to 60% by weight wherein the amount of the solution is sufficient to provide from 1.03 to 1.10 moles of the alkali metal hydroxide or alcoholate per mole of phthalimide;
    (c) removing water and alcohol vapor from the mixing zone; and
    (d) recovering the alkali metal phthalimide.

6. The method of claim 5 wherein the concentration of alcohol is maintained between about 30 and 40% by weight of the mixture.

7. The method of claim 5 wherein the temperature is from 70° to 80° C.

8. The method of claim 6 wherein the temperature is from 70° to 80° C.

9. The method of claim 1 wherein the alcohol is at least one member selected from the group consisting of ethanol, isopropanol and butanol.

10. The method of claim 5 wherein the alcohol is at least one member selected from the group consisting of ethanol, isopropanol and butanol.

11. The method of claim 5 wherein the alcohol concentration in the mixing zone is controlled by removing water and alcohol vapors from the mixing zone.

* * * * *